United States Patent
Seo et al.

(10) Patent No.: US 6,685,644 B2
(45) Date of Patent: Feb. 3, 2004

(54) ULTRASOUND DIAGNOSTIC APPARATUS

(75) Inventors: Yasutsugu Seo, Otawara (JP); Yasuo Miyajima, Utsunomiya (JP); Masaaki Ishiguro, Tokyo (JP)

(73) Assignees: Kabushiki Kaisha Toshiba, Tokyo (JP); Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 10/127,534

(22) Filed: Apr. 23, 2002

(65) Prior Publication Data

US 2002/0173720 A1 Nov. 21, 2002

(30) Foreign Application Priority Data

Apr. 24, 2001 (JP) ........................................ 2001-126242

(51) Int. Cl.[7] ................................................ A61B 8/00
(52) U.S. Cl. ..................................... 600/447; 128/916
(58) Field of Search ................................. 600/463, 117, 600/437, 459–462, 118, 447; 128/916, 899

(56) References Cited

U.S. PATENT DOCUMENTS 5,398,691 A * 3/1995 Martin et al. ............... 600/463
6,120,453 A * 9/2000 Sharp ........................... 600/463
6,203,497 B1 * 3/2001 Dekel et al. ................. 600/439
6,248,074 B1 * 6/2001 Ohno et al. .................. 600/463

FOREIGN PATENT DOCUMENTS

| JP | 10-248852 | 9/1998 |
| JP | 10-277040 | 10/1998 |

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

An ultrasound diagnostic apparatus includes first and second probes. The inside of an object to be examined is scanned with a first ultrasound beam through the first probe to acquire first ultrasound image data associated with the object. The inside of the object is scanned with a second ultrasound beam through the second probe to acquire second ultrasound image data associated with the object. The second ultrasound image data is synthesized with the first ultrasound image data on the basis of the position of the first probe relative to the second probe, which is detected by a position detector.

23 Claims, 5 Drawing Sheets

ULTRASOUND DIAGNOSTIC APPARATUS

CROSS-REFERENCE TO RELATED APPLICATIONS

This application is based upon and claims the benefit of priority from the prior Japanese Patent Application No. 2001-126242, filed Apr. 24, 2001, the entire contents of which are incorporated herein by reference.

BACKGROUND OF THE INVENTION

1. Field of the Invention

The present invention relates to an ultrasound diagnostic apparatus equipped with an internal probe that can be inserted into a body cavity such as a blood vessel or bile duct.

2. Description of the Related Art

Recently, operation of directly inserting an internal probe, for example a small diameter probe inserted into a human body cavity, e.g., a blood vessel or bile duct of a patient, diagnosing a lesion, stricture, and the degree of invasion of a cancer in a tube wall, and determining a surgical operation plan and postoperative therapeutic effect has been done, together with various medical treatments such as TAE (Transcatheter Arterial Embolization), PTCA (Percutaneous Transluminal Coronary Angioplasty), and PTCR (Percutaneous Transluminal Coronary Recanalization). An operator must therefore comprehend the entrance position of a catheter or internal probe and check whether the distal end portion has reached a region to be diagnosed or treated.

Conventionally, a region which a catheter or internal probe enters is imaged by using an X-ray fluoroscopic apparatus, and the operator monitors the position of the distal end of the catheter or internal probe while watching the X-ray image displayed on a monitor. In monitoring by X-ray fluoroscopy, however, the operator is inevitably exposed to X-rays as well as the patient.

For this reason, a method of checking the position of the distal end of a catheter or internal probe by using an ultrasound diagnostic apparatus instead of an X-ray fluoroscopic apparatus has been proposed. The ultrasound diagnostic apparatus is designed to apply ultrasound beams from the body surface to the inside of the body using an external probe, receive an echo signal reflected by a region where acoustic impedance varies, and reconstruct an image. A catheter or internal probe has a smooth surface and is bent inside the body in general. For this reason, ultrasound beams incident from the body surface are regularly reflected by the surface of the catheter or internal probe, and do not return to the body surface probe in many instances. This makes it very difficult to detect a position and form an image. Under the circumstances, a method is disclosed in Jpn. Pat. Appln. KOKAI Publication No. 4-129543, in which a transducer is mounted on the distal end of a catheter or internal probe, and position information is obtained by receiving the ultrasound beam transmitted from an external probe.

A conventional ultrasound diagnostic apparatus is generally designed as a system to reconstruct and display a cross section image by performing scanning within a plane by transmitting ultrasound beams from a one-dimensional array ultrasound transducer. For this reason, attempts have been actively made to obtain 3-D information by acquiring diagnostic images while moving a probe as an ultrasound beam transmitting/receiving unit, and new diagnostic possibility is expected from display of a 3-D image in an ultrasound diagnostic apparatus. In practice, researches have been made by, for example, manually or mechanically moving an abdominal convex probe or linear array probe and using a transesophageal multi-plane probe having a mechanism of rotating an electronic sector probe. However, it takes a considerably long period of time to obtain 3-D information by using the above technique, as compared with the conventional cross section image scanning technique. Hence, movement information cannot be obtained from a target that moves quickly, such as the heart. In addition, if a probe cannot be satisfactorily fixed, even an image of an abdominal portion, which does not move so quickly as the heart, greatly deforms.

Under the circumstances, a 3-D ultrasound diagnostic apparatus is under study, which includes an ultrasound probe having 2-D phased array ultrasound transducers and a function of stereoscopically scanning an ultrasound beam, and can scan and display a 3-D volume image with a corresponding frame.

Conventionally, importance is attached to the resolution of images in an intravascular ultrasound (IVUS) apparatus/intraductal ultrasound (IDUS) apparatus/endoscopic ultrasonography (EUS) apparatus having an internal probe. However, the walls of a blood vessel and body cavity cannot be observed sufficiently deep because of lack of penetration.

BRIEF SUMMARY OF THE INVENTION

It is an object of the present invention to solve the problem associated with the lack of penetration of an ultrasound diagnostic apparatus using an internal probe.

An ultrasound diagnostic apparatus according to the present invention includes first and second probes. The inside of an object to be examined is scanned with a first ultrasound beam through the first probe to acquire first ultrasound image data associated with the object. The inside of the object is scanned with a second ultrasound beam through the second probe to acquire second ultrasound image data associated with the object. The second ultrasound image data is synthesized with the first ultrasound image data on the basis of the position of the first probe relative to the second probe, which is detected by a position detector.

Additional objects and advantages of the present invention will be set forth in the description which follows, and in part will be obvious from the description, or may be learned by practice of the present invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present invention and, together with the general description given above and the detailed description of the embodiments given below, serve to explain the principles of the present invention.

DETAILED DESCRIPTION OF THE INVENTION

First Embodiment

The present invention relates to an ultrasound diagnostic apparatus with an internal probe. There are an ultrasound catheter for the blood vessel to use for IVUS (Intravascular Ultrasound), a small-diameter ultrasound probe for the intradermal duct such as a bile duct and a pancreatic duct to use for IDUS (Intraductal Ultrasound), an ultrasound endoscope to use for a cervical esophagus inspection and so on in the internal probe. It is named as a internal probe including the ultrasound catheter for the blood vessel and the small-diameter ultrasound probe for the intradermal duct.

A internal probe is designed to improve resolution using high frequencies at the sacrifice of penetration (depth of field). The field of view of the internal probe is therefore very narrow. The lack of penetration of the internal probe is compensated by the intracorporeal tissue form information acquired through the external probe placed on the body surface.

Figure 1:
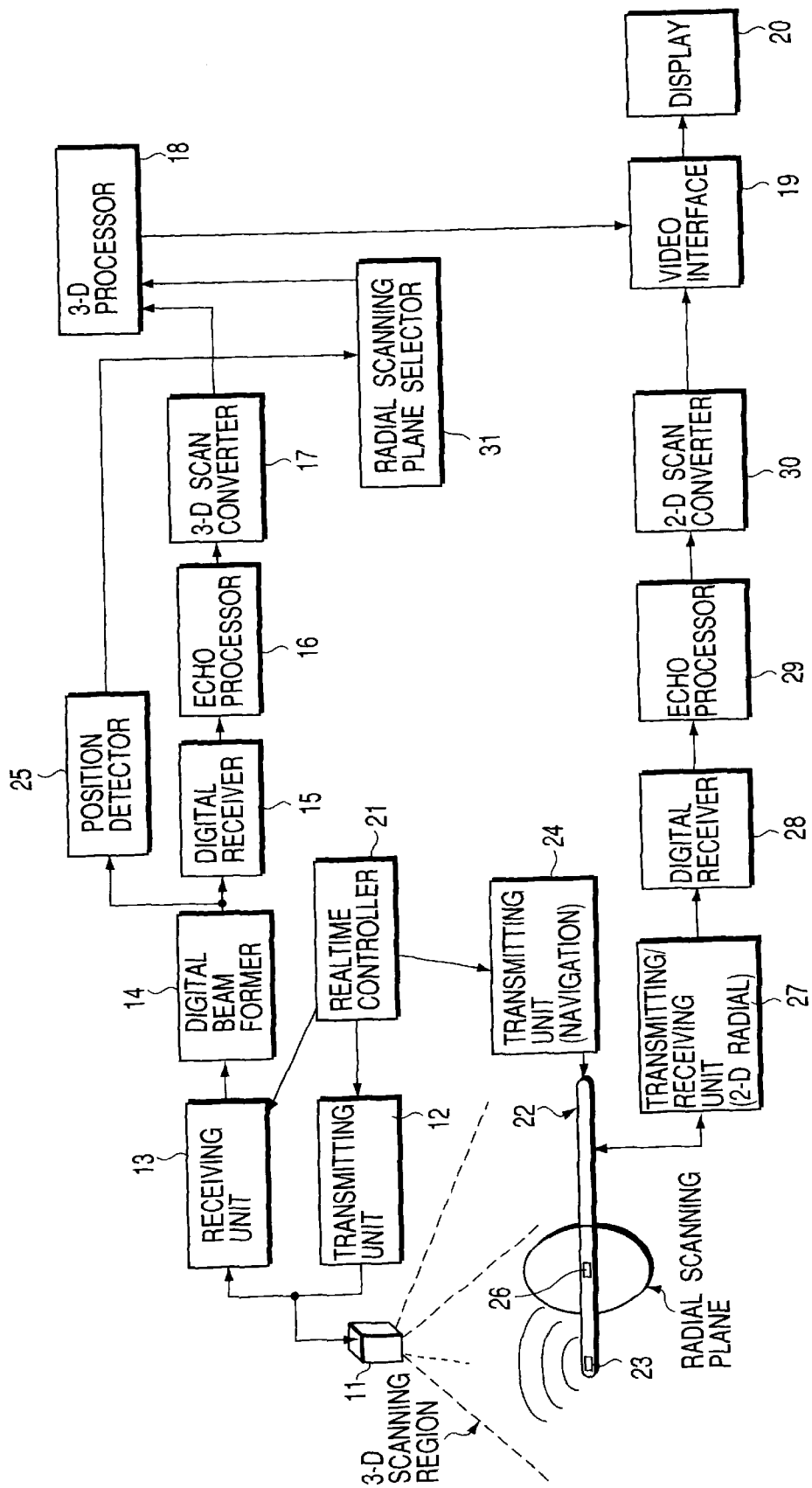
FIG. 1 is a block diagram showing the arrangement of a small-diameter ultrasound diagnostic apparatus according to an embodiment of the present invention.

FIG. 1 shows the arrangement of an ultrasound diagnostic apparatus with a internal probe according to an embodiment of the present invention. This apparatus includes a navigation portion (position detecting unit) for detecting the position of the distal end portion of a internal probe, an external realtime 3-D ultrasound visualizing portion, and an image synthesizing portion as characteristic features in addition to the basic functional portion of the internal probe type ultrasound diagnostic apparatus, i.e., a radial 2-D scanning portion for acquiring a circular tissue form image (to be simply referred to as a radial image hereinafter) by radially (circularly) scanning around the probe through a small transducer (micro-transducer) 26 for 2-D imaging which is mounted in the distal end portion of the internal probe.

(Radial 2-D Scanning Portion)

The small transducer 26 for 2-D imaging is placed near the distal end of a internal probe (first ultrasound probe) 22, and more specifically, behind a navigation transducer 23 at a predetermined distance therefrom. The radial 2-D scanning portion is a unit which is typically designed to obtain a radial 2-D image representing a tissue form by scanning around the probe with a transmitting/receiving unit 27 through the transducer 26 while mechanically and axially rotating the transducer 26. Note that as the center frequency of ultrasound waves for radial 2-D scanning, a frequency is selected from the band of 20 to 50 MHz to obtain relatively high resolution. As the center frequency of ultrasound waves for 3-D scanning by an external probe (second ultrasound probe), a frequency is selected from the band of 1 to 10 MHz to obtain relatively deep penetration. The difference between these center frequencies makes it possible to concurrently execute 3-D scanning and 2-D scanning.

The ultrasound wave generated by the mechanical vibration of the transducer 26 on the basis of a driving signal (high-frequency voltage signal) propagates through an object to be examined, is reflected by a discontinuous surface of acoustic impedance on the way, and returns as an echo to the transducer 26. This echo mechanically vibrates the transducer 26. A weak electrical signal generated by this vibration is amplified by the preamplifier of the transmitting/receiving unit 27 and digitized. The resultant data is subjected to quadrature detection in a digital receiver 28, and is also subjected to envelope detection in an echo processor 29. The ultrasound vector data generated by this operation is converted into circular pixel data by a 2-D scan converter 30. This data is then sent to a video interface 19.

(Navigation Portion)

Figure 2:
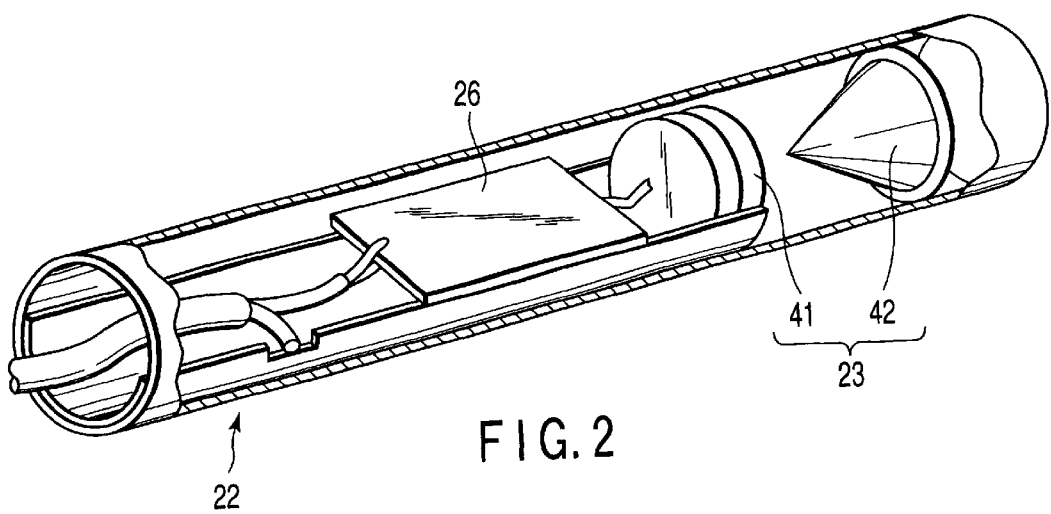
FIG. 2 is a perspective view showing the internal structure of a internal probe in FIG. 1.

This apparatus is equipped with a navigation portion to detect the position of the distal end of the internal probe 22. As shown in FIG. 2, the transducer 23 for navigation is mounted at the distal end of the internal probe 22. A transmitting unit 24 applies a driving signal to the navigation ultrasound wave source 23 in synchronism with the navigation pulse generation signal generated by the realtime controller 21. With this operation, an nondirectional ultrasound pulse is generated from the navigation ultrasound wave source 23. Note that the center frequency of this nondirectional ultrasound pulse is set to a frequency equal or approximate to that of ultrasound waves from an external probe 11 to allow the external probe 11 to detect this nondirectional ultrasound pulse with high sensitivity.

FIG. 2 shows the internal structure of the internal probe 22. A conical reflector 42 is placed in a reversed state inside the distal end portion of the internal probe 22. A transducer 41 is placed to squarely face the reflector 42. The ultrasound wave generated by this transducer 41 is reflected in all directions by the conical reflector 42.

This nondirectional ultrasound pulse propagates in the object to be examined and is received by the external probe 11. A position detector 25 estimates the position of the navigation ultrasound wave source 23, i.e., the position of the distal end of the internal probe 22, on the basis of the reception signal. Obviously, this position is the position of the distal end of the internal probe 22 relative to the external probe 11, and is expressed in a coordinate system unique to the external probe 11 or the XYZ coordinate system with the center of the external probe 11 being set as the origin.

Typical position estimating methods are the GPS scheme and maximum energy pulse detecting scheme. This scheme can use either of these schemes or may selectively use both of them. Alternatively, the two schemes are simultaneously used, and the final position may be determined from the two results (estimated positions).

a) GPS Scheme

The position of the navigation ultrasound wave source 23 seen from the center point of the external probe 11 is estimated by triangulation on the basis of the intensity ratios among three reception signals of navigation ultrasound pulses received at three discrete points on the array surface of the external probe 11, i.e., three discrete transducers or three discrete groups each constituted by a predetermined number of transducers. Theoretically, a position can be estimated by one reception. If, however, the S/N ratio is low, transmission/reception and position estimation may be repeated several times to determine the barycentric position of a plurality of estimated positions as the final position.

b) Maximum Energy Pulse Detection Scheme

The navigation ultrasound pulse received by the external probe 11 is beam-formed in many directions by a digital beam former 14, and the position detector 25 extracts the position of a point on the beam, of these beams, at which the maximum energy (maximum wave height) is obtained. That is, the maximum energy point obtained by scanning the overall volume is the position of the navigation ultrasound pulse source, i.e., the position of the navigation ultrasound wave source 23. This scheme attains a high S/N ratio as compared with the GPS scheme described above. However, since beam forming processing is repeatedly executed in many directions, a long period of time is required for estimation.

(External Realtime 3-D Ultrasound Visualizing Portion)

Figure 3:
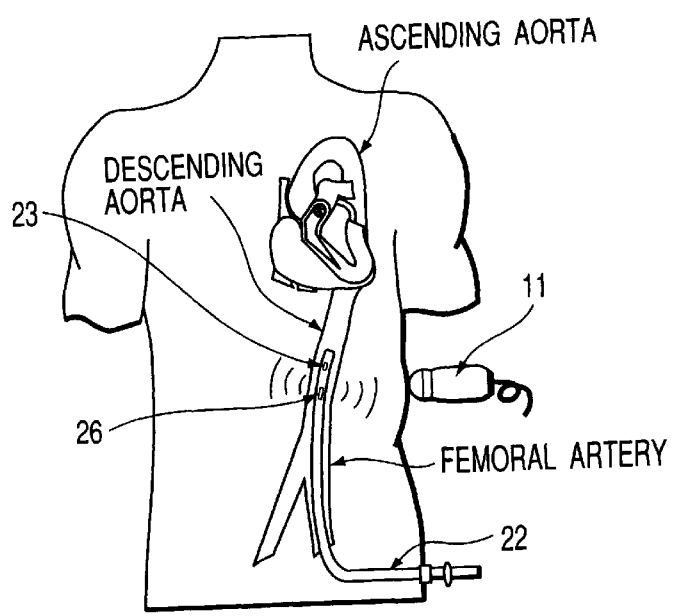
FIG. 3 is a schematic view showing an example of how the internal probe and an external probe in FIG. 1 are used.

The realtime 3-D external probe 11 is a probe of a type that is brought into contact with the body surface of an object to be examined, as shown in FIG. 3, unlike the internal probe 22 inserted into the object. The external probe 11 has a plurality of two-dimensionally arranged transducers to scan a 3-D region inside the object with an ultrasound beam at high speed. A transmitting unit 12 is connected to the external probe 11 at the time of transmission. A receiving unit 13 is connected to the external probe 11 at the time of reception. The transmitting unit 12 has pulsers, transmission delay circuits, and pulse generators respectively connected to a plurality of transducers. Each pulser applies a driving signal (high-frequency voltage signal) to a corresponding transducer in response to a pulse signal, as a trigger, which is generated from a corresponding pulse generator at a predetermined period and delayed by the transmission delay circuit to beam-form an ultrasound sound and give directivity. As the center frequency of this ultrasound wave, for example, a frequency in the band of 1 to 10 MHz, preferably 2.5 MHz or nearby frequency, is selected to obtain relatively deep penetration. The thickness of the piezoelectric element of each transducer is designed accordingly.

Figure 4:
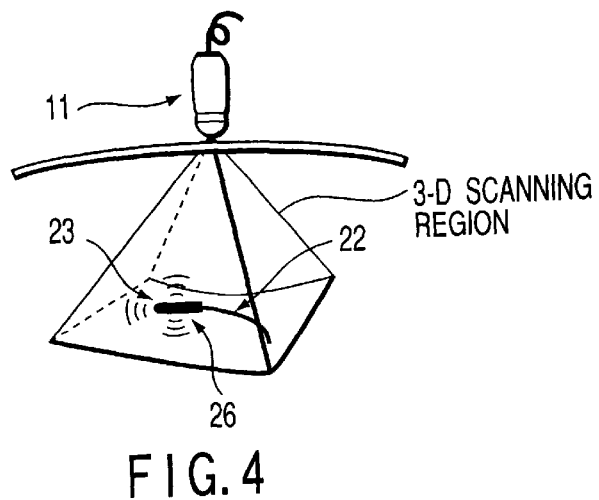
FIG. 4 is a view showing a scanning region for the external probe in FIG. 1.

The ultrasound wave generated by the mechanical vibration of the transducer 26 to which a driving signal is applied propagates through an object to be examined, is reflected by a discontinuous surface of acoustic impedance on the way, and returns as an echo to the probe 11. This echo mechanically vibrates the transducers of the probe 11. A weak electrical signal generated by the vibration is amplified by the preamplifier of the receiving unit 13 and digitized. The resultant data is then subjected to phased addition processing in the digital beam former 14. As a consequence, a reception signal with directivity is generated. As shown in FIG. 4, the transmitting unit 12 and receiving unit 13 change the directivities of transmission and reception for each transmission/reception under the control of the realtime controller 21, thereby scanning a 3-D region in the object with an ultrasound beam. In actual examination, the position of the external probe 11 is adjusted such that a portion near the distal end of the internal probe 22 is included in this 3-D scanning range.

The reception signal generated by the receiving unit 13 is subjected to quadrature detection in a digital receiver 15 and supplied to an echo processor 16. The echo processor 16 performs envelope detection of the reception signal to generate data representing a tissue form. The echo processor 16 also generates bloodstream data from the reception signal through MTI filtering and autocorrelation processing. The bloodstream data contains movement velocity information of bloodstreams and/or power information of bloodstreams. The tissue form data form and The bloodstream data are converted into the volume data of the 3-D region by a 3-D scan converter 17. This data is supplied to a 3-D processor 18.

A radial scanning plane selector 31 calculates the central position and direction of a radial scanning plane on the basis of the axial direction of the internal probe 22 which is specified by the position of the navigation ultrasound wave source 23 detected by the position detector 25 and the axial direction of the internal probe 22 and the temporal displacement of the position, i.e., the traveling direction of the internal probe 22. The radial scanning plane selector 31 then outputs the position and direction data to the 3-D processor 18. The central position of the radial scanning plane is apart from the position of the navigation ultrasound wave source 23, which is detected by the position detector 25, in a direction opposite to the traveling direction by a predetermined distance, i.e., the physical distance between the navigation ultrasound wave source 23 and the transducer 26. The radial scanning plane is perpendicular to the traveling direction with respect to the position of the navigation ultrasound wave source 23.

The 3-D processor 18 reconstructs image data (to be referred to as cross-sectional conversion image data) typically associated with a ring-shaped cross section corresponding to the position and direction of the radial scanning plane. This reconstructed image data is sent to the video interface 19 to be synthesized with radial image data into one frame, which is displayed on the display 20.

The bloodstream data generated by the echo processor 16 is converted into bloodstream 3-D image data by the 3-D processor 18 using a technique such as volume rendering and surface rendering. The 3-D processor 18 adds a marker indicating the position of the navigation ultrasound wave source 23 to this bloodstream 3-D image data in accordance with the position where it is detected.

(Image Synthesizing Portion)

Figure 5:
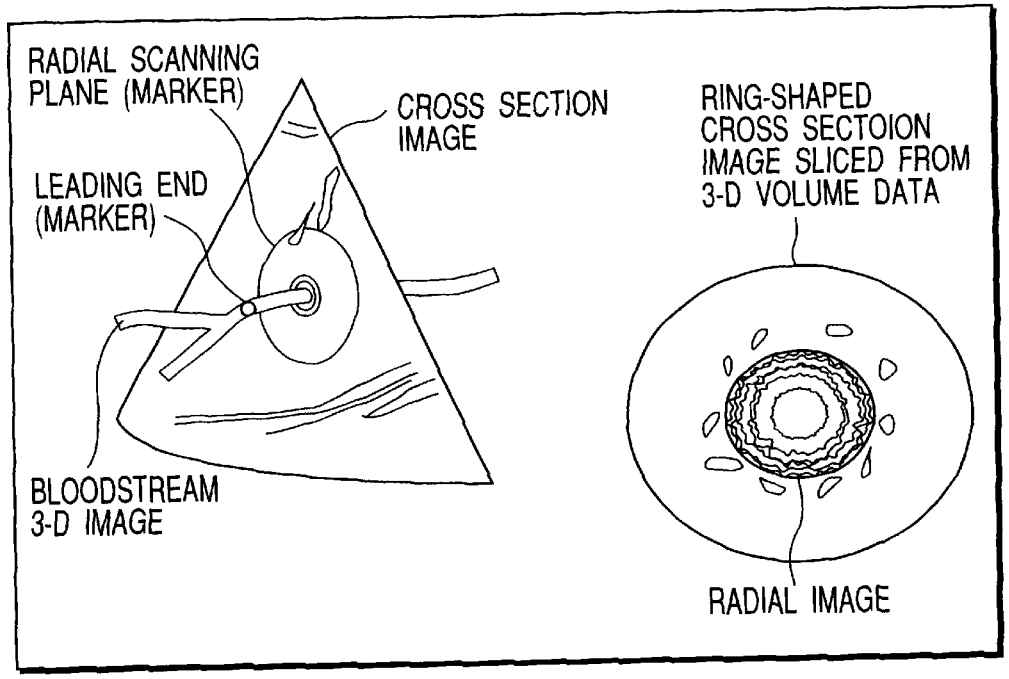
FIG. 5 is a view showing a display example of a display in FIG. 1.

As described above, the video interface 19 synthesizes the radial image from the 2-D scan converter 30 and the ring-shaped image data (cross-sectional conversion image data) representing the tissue form on a cross section flush with the radial scanning plane from the 3-D processor 18, and forms the display window shown in FIG. 5, together with the bloodstream 3-D image data from the 3-D processor 18.

For example, the bloodstream 3-D image is displayed in the left region in the display window. The cross-sectional conversion image data of the radial scanning plane acquired through the external probe 11, a circular marker representing the radial scanning plane, and a marker indicating the position of the navigation ultrasound wave source 23 of the internal probe 22 are synthesized with this bloodstream 3-D image.

In addition, in the right region in the display window, the radial image representing the tissue form obtained through the 2-D imaging transducer 26 of the internal probe 22 is displayed. the cross-sectional conversion image data reconstructed by the 3-D processor 18 is synthesized with this radial image to compensate for the lack of penetration. Thereby the image that the ultrasound image by the internal probe 22 is superimposed on the ultrasound image by the external probe 11 is obtained.

Figure 6A:
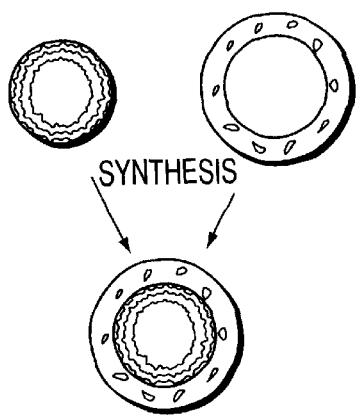
FIG. 6A is a view showing the first method of synthesizing a radial image with an image sliced from volume data.
Figure 6B:
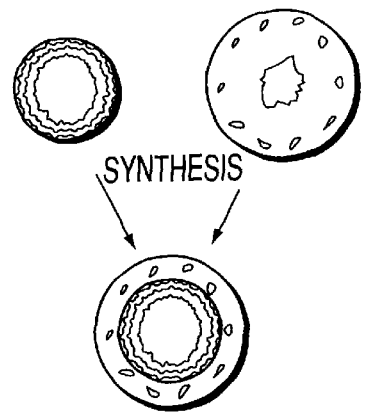
FIG. 6B is a view showing the second method of synthesizing a radial image with an image sliced from volume data.

The cross-sectional conversion image to be synthesized with this radial image may be a ring-shaped range in contact with the outer circumference of the radial scanning plane of the internal probe 22 as shown in FIG. 6A or a range which includes the radial scanning surface of the internal probe 22 is concentric therewith as shown in FIG. 6B. The operator can arbitrarily select one of them.

By synthesizing the radial image of the internal probe 22 with the form image (cross-sectional conversion image) acquired from a surrounding image through the external probe 11 in this manner, the lack of penetration of the internal probe 22 can be compensated to allow the operator to see a sufficiently deep portion in a blood vessel wall.

Figure 7:
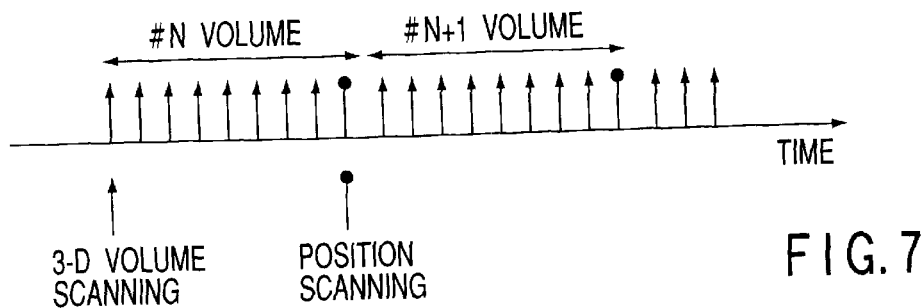
FIG. 7 is a view showing a sequence of 3-D volume scanning and position scanning.

FIG. 7 shows a sequence of 3-D volume scanning by the external probe 11 and position scanning, in which an non-directional ultrasound wave is transmitted from the transducer 23 and is received by the external probe 11 to detect the position of the source 23 of the internal probe 22 (the position of the distal end of the catheter), in this embodiment. As described above, since ultrasound waves in the same frequency band are used in these operations, the operations must be performed time-divisionally. In this case, position scanning is executed once every time volume scanning is repeated a predetermined number of times, e.g., eight times.

Figure 8:
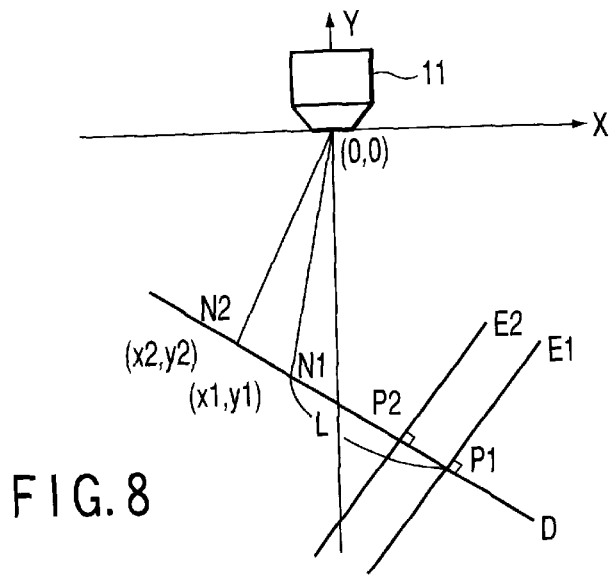
FIG. 8 is a view for explaining a method of computing the position and direction of the internal probe relative to the external probe by using a position detector in FIG. 1.

FIG. 8 is a view for explaining detection of the position of the transducer 23 of the internal probe 22 (the position of the distal end of the catheter) by the position detector 25. The central position of the external realtime 3-D ultrasound probe 11 is set as the origin (0, 0) on the X- and Y-axes. Let N1 be the position (x1, y1) of the navigation ultrasound wave source 23 mounted on the distal end of the catheter at time t1, P1 be the position of the radial scanning transducer 26 mounted at the central portion of the catheter at time t1, L be the fixed distance between the navigation ultrasound wave source 23 and the radial scanning transducer 26, N2 be the position (x2, y2) of the position of the navigation ultrasound wave source 23 at time t2 after the lapse of a position scanning period from time t1, and P2 be the position of the radial scanning transducer 26. The catheter therefore travels from N1 to N2 (from P1 to P2). Letting D be a line connecting N1 and N2 (P1 and P2), a line E1 perpendicular to the line D corresponds to a plane in which a cross section (radial scanning plane) of the image obtained by the radial scanning transducer 26 of the catheter is contained. Likewise, let E2 be a cross section after a given period of time.

Information on the cross sections E1 and E2 must be sliced from the volume data acquired by the external realtime 3-D probe 11, and the position and direction of each cross section are computed by the radial scanning plane selector 31 in FIG. 1. The computation result or volume data on the corresponding cross section represented by the computation result is sent to the video interface 19.

An example of the computation method will be described below.

The slope of the straight line D is given by (y2−y1)/(x2, x1). The slopes of the straight lines E1 and E2 are perpendicular to the straight line D, and hence are given by (x2−x1)/(y2−y1).

If the straight line E2 is given by $$y = \frac{x_2 - x_1}{y_2 - y_1}x + b$$

since the straight line E2 passes through the point P2, the coordinates of the point P2 are given by $$\left(x_2 + \frac{(x_2 - x_1)L}{\sqrt{(y_2 - y_1)^2 + (x_2 - x_1)^2}}, y_2 + \frac{(y_2 - y_1)L}{\sqrt{(y_2 - y_1)^2 + (x_2 - x_1)^2}}\right)$$

In addition, according to $$b = -\frac{x_2 - x_1}{y_2 - y_1} \cdot \left(x_2 + \frac{(x_2 - x_1)L}{\sqrt{(y_2 - y_1)^2 + (x_2 - x_1)^2}}\right) + y^2 + \frac{(y_2 - y_1)L}{\sqrt{(y_2 - y_1)^2 + (x_2 - x_1)^2}}$$

the straight line E2 is expressed by $$y = \frac{x_2 - x_1}{y_2 - y_1}x - \frac{x_2 - x_1}{y_2 - y_1} \cdot \left(x_2 + \frac{(x_2 - x_1)L}{\sqrt{(y_2 - y_1)^2 + (x_2 - x_1)^2}}\right) + y^2 + \frac{(y_2 - y_1)L}{\sqrt{(y_2 - y_1)^2 + (x_2 - x_1)^2}}$$

According to this relational expression, position data on the straight line E2 can be read.

According to this embodiment, as described above, the radial image obtained by the internal probe 22 is synthesized with a surrounding image sliced from the 3-D volume data acquired through the external probe 11. This compensates for the lack of penetration of the internal probe 22 and allows the operator to see a sufficiently deep portion of a blood vessel wall.

Second Embodiment

In the second embodiment, cylindrical 3-D volume data is generated from the radial image acquired by a internal probe 22, and the data acquired by an external realtime 3-D probe 11 is synthesized with the outer circumference of this cylindrical region. The 3-D volume data of a large cylindrical region can be generated by synthesizing the data acquired by the internal probe 22 and the data acquired by the external probe 11.

Figure 10:
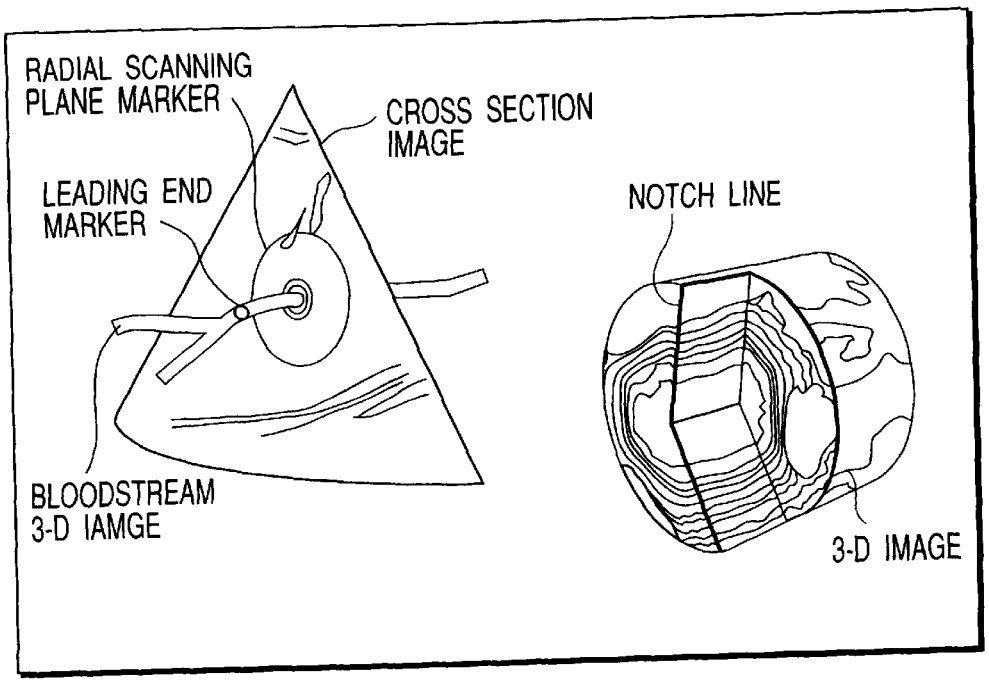
FIG. 10 is a view showing a display example of a display corresponding to the arrangement shown in FIG. 9.
Figure 9:
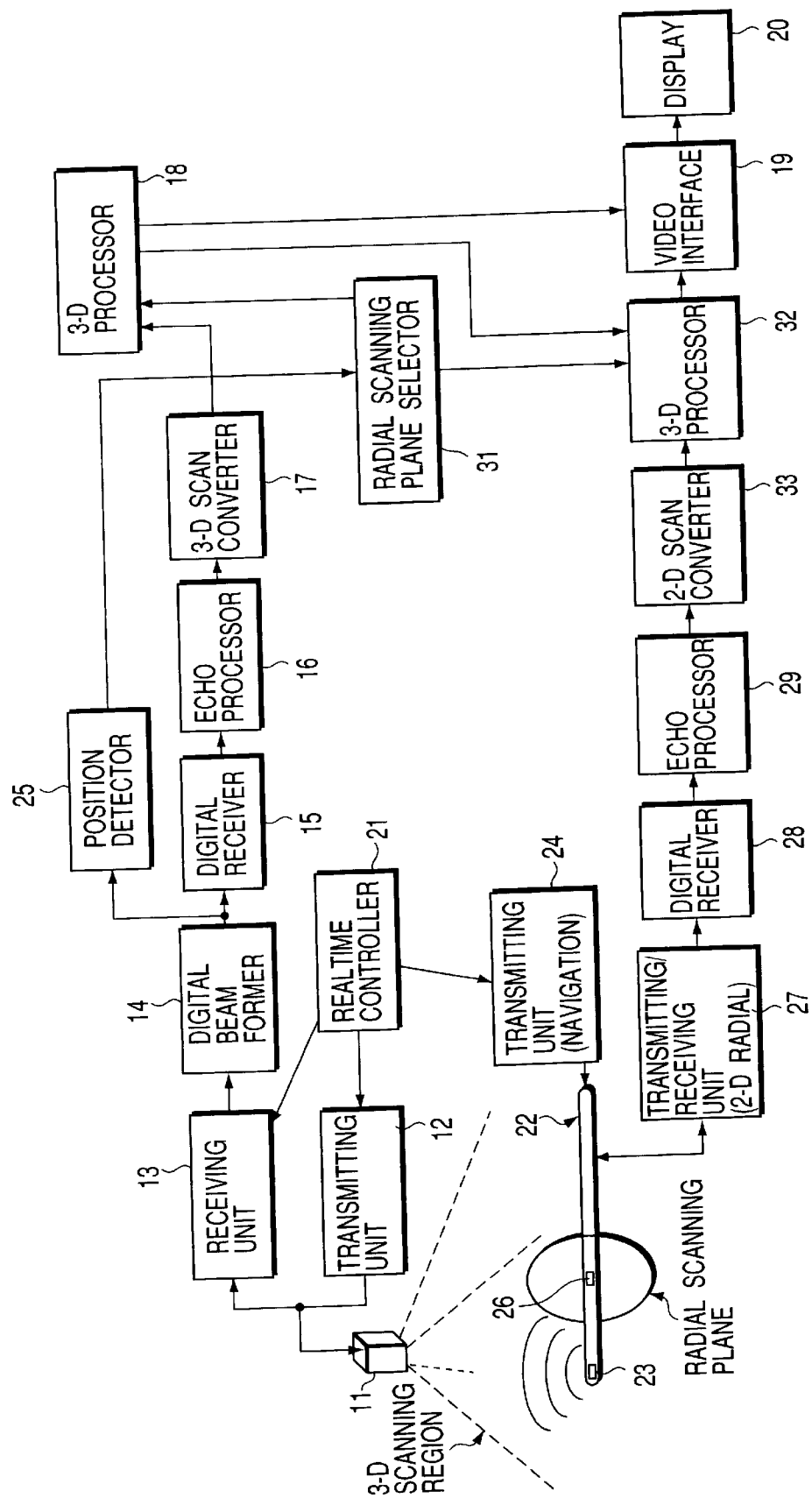
FIG. 9 is a bock diagram showing another example of the arrangement of the internal probe type ultrasound diagnostic apparatus according to the embodiment of the present invention.

FIG. 9 shows an arrangement of this embodiment. FIG. 10 shows a display example. A 3-D processor 32 has a 3-D volume memory and generates cylindrical 3-D volume data by writing the data output from a 2-D scan converter 29 and 3-D processor 18 in this 3-D volume memory.

More specifically, the 2-D scan converter 29 and a radial scanning plane selector 31 respectively send a radial image and the position information of a cross section to the 3-D processor 18. The 3-D processor 18 slices the data of the cross section from the 3-D volume data obtained by the external probe 11, and sends the data to the 3-D processor 32. The 3-D processor 32 writes the data of the radial image at an address corresponding to the position of the cross section in the 3-D volume memory. At this time, the 3-D processor 32 writes the data sent from the 3-D processor 18 in the outer circumference of the radial image. With this operation, the circular data obtained by synthesizing the data, acquired by the external probe 11, with the outer circumference of the radial image is written in the 3-D volume memory.

This operation is performed for each frame sequentially output from the 2-D scan converter 29. With this operation, the above synthesized circular data are sequentially written at the positions of the corresponding cross sections, thereby generating the 3-D volume data of a cylindrical ultrasound image.

The 3-D processor 32 obtains a 3-D image to be displayed from the above cylindrical 3-D volume data by performing processing such as volume rendering and surface rendering. In this case, it is preferable that an arbitrary portion of the cylindrical 3-D volume data be cut away to allow observation of the state of the inside of the cylinder.

This display image is sent from the 3-D processor 32 to a video interface 19 to be synthesized with the surface image data originated from the external probe and generated by the 3-D processor 18.

FIG. 10 shows an example of the image displayed on a display monitor 20 at this time. The image obtained by synthesizing the cross section image corresponding to a radial scanning plane, generated on the basis of the data acquired from the external probe 11, a bloodstream 3-D image, a circular marker indicating the radial scanning plane, and a marker indicating the position of a navigation transducer 23 of the internal probe 22 is displayed on, for example, the left area on the display screen.

In addition, the image obtained by synthesizing the cylindrical 3-D form image data acquired by the external probe 11 with the outer circumference of the cylindrical 3-D radial image data representing a tissue form, acquired by a 2-D imaging transducer 26 of the internal probe 22 is displayed on the right area on the display screen. The 3-D image obtained by cutting away a portion of this cylindrical 3-D form image data is displayed.

With this operation, high-resolution 3-D image data is obtained by the internal probe 22 to allow proper observation of the state of the tissue. The lack of penetration of the internal probe 22 is compensated by the data obtained by the external probe 11 to generate 3-D image data in a wide range, thereby allowing the operator to properly grasp the relationship between the tissue positions. In addition, since the 3-D image obtained by cutting away an arbitrary portion of this 3-D image data can be displayed, the operator can properly observe a desired portion inside a blood vessel by changing this cut portion.

As described above, an image originated from the external probe may be synthesized with an image originated from the internal probe on three dimensions, and the resultant image may be displayed.

Note that the present invention is not limited to the above embodiment, and can be variously modified and practiced within the sprit and scope of the invention. The above embodiments include inventions of various stages, and various inventions can be extracted by proper combinations of a plurality of disclosed constituent elements. For example, several constituent elements can be omitted from the all the constituent elements in the embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnostic apparatus comprising:
a first probe;
a second probe;
a first transmitter/receiver configured to scan the inside of an object to be examined with a first ultrasound beam through said first probe to acquire first ultrasound image data associated with the object;
a second transmitter/receiver configured to scan the inside of the object with a second ultrasound beam through said second probe to acquire second ultrasound image data associated with the object;
a position detector configured to detect a position of said first probe relative to said second probe;
a first converter configured to receive and store the first ultrasound image data and positional information related to the first ultrasound image data;
a second converter configured to receive and store the second ultrasound image data and positional information related to the second ultrasound image data;
an image processor configured to synthesize the second ultrasound image data from the second converter with the first ultrasound image data from the first converter on the basis of the detected position to generate synthetic image data; and
a display configured to display an image on the basis of the synthetic image data.

2. An apparatus according to claim 1, wherein said first probe is placed inside the object, and said second probe is placed outside the object.

3. An apparatus according to claim 1, wherein said first probe is of a radial scanning type, and said second probe is of a 3-D scanning type.

4. An apparatus according to claim 1, wherein said second transmitter/receiver scans a 3-D region inside the object through said second probe to acquire volume data.

5. An apparatus according to claim 4, wherein said image processor generates cross section image data of a cross section corresponding to the position of said first probe from the volume data, and synthesizes the cross section image data with the first ultrasound image data.

6. An apparatus according to claim 1, wherein said image processor superimposes the first ultrasound image data on the second ultrasound image data upon position matching on the basis of the detected position.

7. An apparatus according to claim 1, wherein said image processor generates image data of a cross section corresponding to the detected position from the second ultrasound image data.

8. An apparatus according to claim 1, wherein a center frequency of the first ultrasound beam differs from a center frequency of the second ultrasound beam.

9. An apparatus according to claim 1, wherein a center frequency of the first ultrasound beam is higher than a center frequency of the second ultrasound beam.

10. An apparatus according to claim 1, wherein scanning of the first ultrasound beam is executed concurrently with scanning of the second ultrasound beam.

11. An apparatus according to claim 1, wherein said position detector includes an nondirectional vibrator mounted on said first probe, and a position calculator which calculates the position of said first probe on the basis of a reception signal transmitted from said nondirectional vibrator and received by said second probe.

12. An apparatus according to claim 11, wherein said position calculator calculates a traveling direction of said first probe on the basis of a change in the position of said first probe.

13. An apparatus according to claim 1, wherein a center frequency of an nondirectional ultrasound wave transmitted from said nondirectional vibrator is substantially equal to a center frequency of the second ultrasound beam transmitted from said second probe.

14. An apparatus according to claim 1, further comprising a unit configured to acquire volume data associated with a bloodstream inside the object through said second probe, and a unit configured to generate 3-D image data associated with a bloodstream from the volume data.

15. An apparatus according to claim 14, wherein said display unit displays the synthesized ultrasound image data, together with the 3-D image data.

16. An apparatus according to claim 15, wherein a marker representing the position of said first probe is displayed together with the 3-D image data.

17. An ultrasound diagnostic apparatus comprising:

a internal probe which is inserted into the body of an object to be examined;

an external probe which is brought into contact with a body surface of the object;

a unit configured to acquire radial cross section image data by radial scanning around said internal probe with the first ultrasound through said internal probe;

a unit configured to acquire volume data by scanning a 3-D region inside the object with the second ultrasound beam through said external probe;

a first converter configured to receive and store the radial cross section image data and positional information related to the radial cross section data;

a second converter configured to receive and store the volume data and positional information related to the volume data;

an image processor configured to generate cross section image data of a cross section corresponding to the position of said internal probe from the volume data and performing synthesis of the cross section image data from the second converter with the radial cross section image data from the first converter; and a display configured to display an image on the basis of the image data obtained by the synthesis.

18. An apparatus according to claim 17, wherein said image processor generates cross section image data associated with a ring-shaped cross section from the volume data.

19. An apparatus according to claim 17, wherein said image processor generates cross section image data associated with a circular cross section from the volume data.

20. An apparatus according to claim 17, further comprising a position detector configured to detect a position of said internal probe relative to said external probe.

21. An apparatus according to claim 20, wherein said position detector includes a nondirectional vibrator mounted on said internal probe, and a unit which calculates the position of said internal probe on the basis of a reception signal transmitted from said nondirectional vibrator and received by said external probe.

22. An image generating method for an ultrasound diagnosis comprising:

generating first ultrasound image data on the basis of outputs of an internal probe;

generating second ultrasound image data on the basis of outputs of an external probe;

transmitting said first ultrasound image data and positional information related to said first ultrasound image data to a first converter;

transmitting said second ultrasound image data and positional information related to said second ultrasound image data to a second converter;

detecting a position of said internal probe relative to said external probe; and synthesizing the second ultrasound image data from the second converter with the first ultrasound image data from the first converter on the basis of the detected position to generate a display image data.

23. A method according to claim 22, wherein the display image data is generated from 3-D volume data formed by a composition with the first ultrasound image and the second ultrasound image.

* * * * *